United States Patent
Rolland et al.

(10) Patent No.: US 10,111,917 B2
(45) Date of Patent: Oct. 30, 2018

(54) **METHOD FOR PREPARING PURIFIED EXTRACTS OF *HARPAGOPHYTUM PROCUMBENS***

(75) Inventors: Yohan Rolland, Macon (FR); Charles Duval, Charnay les Macon (FR)

(73) Assignee: NATUREX, Avignon (FR)

( * ) Notice: Subject to any disclaimer, the term of this patent is extended or adjusted under 35 U.S.C. 154(b) by 444 days.

(21) Appl. No.: 12/599,146

(22) PCT Filed: Apr. 28, 2008

(86) PCT No.: PCT/FR2008/050769
§ 371 (c)(1),
(2), (4) Date: Aug. 20, 2010

(87) PCT Pub. No.: WO2008/145931
PCT Pub. Date: Dec. 4, 2008

(65) Prior Publication Data
US 2010/0311675 A1    Dec. 9, 2010

(30) Foreign Application Priority Data
May 7, 2007   (FR) ..................................... 07 54906

(51) Int. Cl.
*A61K 36/185*   (2006.01)
(52) U.S. Cl.
CPC .................................. *A61K 36/185* (2013.01)
(58) Field of Classification Search
None
See application file for complete search history.

(56) References Cited

U.S. PATENT DOCUMENTS

| | | | |
|---|---|---|---|
| 6,280,737 B1 * | 8/2001 | Stumpf et al. | 424/769 |
| 6,395,308 B1 | 5/2002 | Berkulin et al. | |
| 6,812,214 B2 * | 11/2004 | Shin et al. | 514/27 |
| 2002/0183264 A1 | 12/2002 | Shin et al. | |

FOREIGN PATENT DOCUMENTS

| | | | |
|---|---|---|---|
| DE | 196 03788 | | 8/1997 |
| DE | 10310267 A1 | * | 9/2004 |
| GB | 2335919 A | * | 10/1999 |
| KR | 920 005 686 | | 7/1992 |
| KR | 9205686 B | * | 7/1992 |
| KR | 2002041709 A | * | 6/2002 |

OTHER PUBLICATIONS

Kikuchi et al. Chem. Pharm. Bull. vol. 31, No. 7(1983), 2296-2301.*
U.S. Department of Health and Human Services Food and Drug Administration Center for Drug Evaluation and Research (CDER) Center for Biologics Evaluation and Research (CBER). "Guidance for Industry Q3C—Tables and List" (2012). Retrieved from the internet: https://www.fda.gov/downloads/drugs/guidances/ucm073395.pdf>.*
Schmidt A H: "Fast HPLC for quality control of Harpagophytum procumbens by using a monolithic silica column: method transfer from conventional particle-based silica column", Journal of Chromatography A, Elsevier, Amsterdam, NL, vol. 1073, No. 1-2, (May 6, 2005), pp. 377-381.
Gunther M et al: "High anti-inflammatory activity of harpagoside-enriched extracts obtained from solvent-modified super- and subcritical carbon dioxide extractions of the roots of Harpagophytum procumbens", Phytochemical Analysis, XX, XX, vol. 17, No. 1, (Jan. 2006), pp. 1-7.
Faivre C et al: "Grapple plant or devil's claw. Harpagophytum procumbens (Pedaliaceae)", Phytotherapie, Springer-Verlag, Paris, FR, vol. 5, No. 3, 2007, pp. 150-153.

* cited by examiner

*Primary Examiner* — Amy L Clark
(74) *Attorney, Agent, or Firm* — Stephen J. Weyer, Esq.; Stites & Harbison, PLLC

(57) ABSTRACT

A method for preparing a concentrated extract of *Harpagophytum procumbens*, in liquid or dry form, having a harpagoside titer greater than or equal to 5%, comprises a step of purifying a crude extract of *Harpagophytum procumbens* in liquid form in aqueous phase by a technique of liquid-liquid extraction with an organic solvent selected from the esters.

11 Claims, No Drawings

METHOD FOR PREPARING PURIFIED EXTRACTS OF *HARPAGOPHYTUM PROCUMBENS*

The present invention relates to a method for preparing purified extracts of *Harpagophytum procumbens*, said extracts being in liquid or dry form.

The present invention relates also to purified extracts as obtained by said method.

*Harpagophytum* (*Harpagophytum procumbens*) is a plant native to South Africa which is traditionally known for its efficacy in the treatment, inter alia, of arthrosis pain.

Its tuberous lateral roots contain in particular compounds of the iridoid type, glycosylated or unglycosylated, which are considered to be the active ingredients and are called harpagoside, harpagide, procumbide and procumboside.

Modern phytotherapy uses plant powder or plant extracts in galenical formulations in dry form of the gelatin capsule type. The use of plant powder means that a very large number of doses must be taken per day, which is very restricting on a daily basis.

The food supplement and phytotherapy industries now have available a large number of plant extracts for these applications.

*Harpagophytum* extracts are usually obtained using aqueous alcoholic solvents, it being possible for the alcohol titre to vary from 0 (extract with water) to 90% (Chrubasik S.; Devil's claw extract as an example of the effectiveness of herbal analgesics; Orthopade. 2004 July; 33(7): 804-808).

The European Pharmacopoeia also describes, in the monograph of the *Harpagophytum* root, the use of methanol for the extraction of harpagoside.

The plant is separated from the extraction solvent by any conventional process, for example of the filtration or centrifugation type. Where an alcoholic solvent is used, the solvent is removed from the filtrate, and the filtrate is optionally concentrated in order to reduce the volume and then dried.

This type of process makes it possible to obtain *harpagophytum* extracts having a harpagoside titre of approximately from 2.5 to 3%, measured by HPLC. In addition, variation of the usual parameters of the vegetal extraction, such as the nature of the solvent, the temperature and duration of the extraction, has no effect on the final titre of the resulting powder. A titre of about 2.5 to 3% is always obtained.

Products having a harpagoside titre of from 2.5 to 3% by HPLC offer a satisfactory alternative to the use of plant powder to produce gelatin capsules but do not enable the dosage to be reduced significantly for the treatments for which *harpagophytum* is effective.

Only products having a higher harpagoside titre would be able to limit the daily dose of gelatin capsules significantly.

Therefore, there is a lack of a method which allows powdered *harpagophytum* extracts to be obtained industrially with high harpagoside titres.

Among the means described for obtaining such a result, and even though, given the polarity of the molecule, the person skilled in the art is not immediately drawn to this solution, mention may be made of the use of super- or sub-critical fluid (Gunther M, Laufer S, Schmidt PC. High anti-inflammatory activity of harpagoside-enriched extracts obtained from solvent-modified super- and subcritical carbon dioxide extractions of the roots of *Harpagophytum procumbens*; Phytochem Anal. 2006, January-February; 17(1): 1-7).

Extractions of *Harpagophytum procumbens* roots with carbon dioxide/solvent modified have been studied in respect of the extraction efficiency and the harpagoside content and have been compared with a conventional extract.

The effects of the pressure, the temperature and the type and concentration of the modifying agent were examined. Two extraction steps were necessary to obtain anti-inflammatory extracts that were greatly enriched with harpagoside. The first extraction step was carried out in the supercritical state using carbon dioxide modified with n-propanol to remove the undesirable lipophilic substances. The main extraction was carried out in the supercritical or subcritical state with carbon dioxide modified with ethanol. The supercritical liquid extraction yielded extracts containing up to more than 30% harpagoside. The subcritical extracts exhibited a harpagoside content of 20%, but the extraction yield was almost three times greater than under supercritical conditions.

The level of recovery of harpagoside, given by the sum of the extract and the crude residue, was 99% greater than in all the preceding experiments. The conventional extract and two carbon dioxide extracts were examined for the in vitro inhibition of 5-lipoxygenase, or 2-cyclooxygenase biosynthesis. The two carbon dioxide extracts exhibited total inhibition of the biosynthesis of 5-lipoxygenase at a concentration of 51.8 mg/l; in contrast, the conventional extract does not exhibit inhibition of 5-lipoxygenase biosynthesis.

The value of purified extracts of *harpagophytum* root is clearly demonstrated here. However, it is necessary to replace this type of super- or sub-critical $CO_2$ extract in an industrial context. The extracts obtained by means of $CO_2$ are in a very high price range, much higher than extracts by means of solvent, and this type of process requires very large installations, given the very high pressures that are employed.

The products obtained by $CO_2$ extraction are not generally in powder form but rather in the form of a paste or wax, which is not compatible with the production of gelatin capsules, for example, or may be adsorbed on a support, which reduces the titre of the product. In addition, the products so obtained are liposoluble extracts and are therefore insoluble in aqueous phases. Finally, it is pointed out that this type of process using $CO_2$ results in compounds of the pesticide and mycotoxin type, and therefore concentrates them in the finished product. Accordingly, $CO_2$ extractions do not permit the preparation of *harpagophytum* extracts having a high harpagoside titre that are compatible with all liquid or dry galenical formulations.

Accordingly, it is an object of the present invention to provide an industrially applicable method for preparing purified extracts of *harpagophytum* having a high harpagoside titre, said extracts so obtained being compatible with all liquid (syrups or capsules) or dry (tablets or gelatin capsules) galenical formulations.

It is also an object of the present invention to provide *harpagophytum* extracts which have a high harpagoside titre and are soluble in aqueous phases.

The present invention relates to a method for preparing a concentrated extract of *Harpagophytum procumbens*, in liquid or dry form, having a harpagoside titre greater than or equal to 5%, preferably greater than or equal to 35%, which method comprises a step of purifying a crude extract of *Harpagophytum procumbens* in liquid form in an aqueous phase using a technique of liquid-liquid extraction with an organic solvent selected from the esters, especially the aliphatic esters, and more particularly from the alkyl acetates, said alkyl group being a branched or linear alkyl chain having from 1 to 10, especially from 1 to 6 and preferably from 1 to 4 carbon atoms.

Accordingly, the present invention is based on the fact that the inventors have found that iridoid glucosides of *harpagophytum* can, surprisingly, be purified by means of solvents of the ester type.

The use of solvents such as alcohols and ketones is known at present.

Although the Snyder polarity ranks ethyl acetate (4.1) on the same level as ethanol (4.3) but lower than methanol (5.1) and acetone (5.1) and slightly higher than butanol (3.9), the dielectric constant of ethyl acetate ($\varepsilon=6$) is extremely low and does not suggest at all that ethyl acetate may create affinity bonds with polar molecules, thus solubilizing them and a fortiori purifying molecules of the iridoid glucoside type.

Surprisingly, esters such as ethyl acetate are very selective in respect of this type of compound and permit very efficient purifications to titres greater than 35% on a dry basis.

Among all the pitfalls encountered during the production of a *harpagophytum* extract, there is the difficulty associated with degradation of the active ingredients. Accordingly, the person skilled in the art uses solvents such as water or alcohols to prepare the crude extracts, and solvents such as alcohols and aliphatic ketones to purify them.

If such extracts are prepared under conventional conditions (extraction, removal of the organic solvent in vacuo if necessary, concentration to obtain a crude extract, which can be dried or purified by means of a different organic solvent, followed by removal of the organic solvent in vacuo, concentration and drying), harpagoside titres below 3% are always obtained. The intermediate products are much more concentrated, but the different steps lead to gradual degradation of the active ingredients.

Among the improvements that have been proposed there may be mentioned drying in an organic solvent phase (alcohol or butanol) (as described, for example, in U.S. Pat. No. 6,280,737), which requires equipment that is very expensive and does not perform very well. In all cases, the harpagoside titres of the extracts so obtained are 20% at the maximum.

The use of a water-immiscible organic solvent of the butanol type for the purification of *harpagophytum* extracts also presents the problem of the temperature imposed on the product in order to remove said organic solvent. Butanol on its own boils at 117° C. at ambient temperature, and the water/butanol mixture encountered during the purification steps boils at 92.6° C. Even under conditions of evaporation—drying in vacuo, the product is exposed to a high temperature, which leads to degradation of the active ingredients.

The use of a water-immiscible solvent of the ester type allows the operations of evaporation—drying to be carried out at a much lower temperature and therefore enables degradation of the active ingredients to be limited. Accordingly, the use of esters having a boiling point below that of the alcohols used in the prior art (especially butanol) allows the product (active ingredient—harpagoside) not to be exposed to high temperatures, which allows the duration of the process exposing the product to high temperatures to be reduced. Thermal degradation of the active ingredient does not take place, and high titres of the resulting purified extracts can be retained (up to at least 35%).

In addition, because the product can be concentrated at low temperature, it is possible to prepare a concentrate in aqueous phase that is devoid of the organic solvent fraction and make a gain in productivity in the drying step, which can be carried out on equipment that is standard and therefore less expensive and therefore of better dimensions. Lyophilization can be a drying means that is used, for example.

The harpagoside titre mentioned above is a weight/weight (w/w) titre expressed based on the total weight of dry matter.

It is measured by the method of the European pharmacopoeia 5.07, as follows: the procedure used is liquid chromatography using methyl cinnamate as internal standard.

Preparation of the Internal Standard Solution:

0.130 g of methyl cinnamate is dissolved in 50 ml of methanol and made up to 100.0 ml with the same solvent.

Preparation of the Solution to be Analyzed:

50 ml of methanol are added to 0.500 g of powdered *harpagophytum* (*Harpagophytum procumbens*) root. Stirring is carried out for 1 hour, followed by filtration. The residue is then transferred to a 100 ml flask, 50 ml of methanol are added, and the mixture is heated at reflux for 1 hour. The whole is then cooled and filtered. The flask and the filter are then washed with 2×5 ml of methanol. The extracts are then combined and evaporated to dryness under reduced pressure and at a temperature not exceeding 40° C. The residue is then treated with 3×5 ml of methanol, and the extracts are filtered in a 25 ml volumetric flask. The filter is washed, and the mixture is made up to 25.0 ml with methanol. 1.0 ml of internal standard solution is added to 10.0 ml of that solution, and the mixture is made up to 25.0 ml with methanol.

Preparation of the Control Solution:

0.5 ml of control solution (1 mg of harpagoside in 1 ml of methanol) are removed and made up to 2.0 ml with methanol.

Chromatography can be carried out, for example, using:
  a stainless steel column having a length of 0.10 m and an inside diameter of 4 mm, filled with octadecylsilylated silica gel for chromatography (5 μm),
  as mobile phase, at a flow rate of 1.5 ml/minute, a mixture of equal volumes of water and methanol,
  as detector, a spectrophotometer set at 278 nm,
  and a 10 μl loop injector.

Analysis by Chromatography:

the solution to be examined is injected and the sensitivity of the system is adjusted so that the height of the peak corresponding to methyl cinnamate represents 50% of the total scale of the recorder.

The harpagoside retention time is determined using 10 μl of control solution examined under the same conditions as the solution to be examined. The harpagoside content (%) is then calculated using the expression:

$$\frac{m_2 \times F_1 \times 7{,}622}{F_2 \times m_1}$$

where $m_1$=mass of the test portion (g)
  $m_2$=mass of the methyl cinnamate (g) in the internal reference solution
  $F_1$=area of the peak corresponding to harpagoside in the chromatogram obtained with the solution to be analyzed
  $F_2$=area of the peak corresponding to methyl cinnamate in the chromatogram obtained with the solution to be analyzed.

According to a particular embodiment, the present invention relates to a method for preparing a concentrated extract of *Harpagophytum procumbens*, in liquid or dry form, having a harpagoside titre greater than or equal to 5%, which method comprises the following steps:
- a purification step of the type liquid-liquid extraction between a crude extract of *Harpagophytum procumbens* in liquid form in aqueous phase and an organic solvent selected from the esters, in order to obtain an aqueous phase and a harpagoside-concentrated organic phase,
- a step of removal of the solvent from the organic phase obtained previously, in order to obtain said concentrated extract in liquid form, and
- an optional step of conversion of said concentrated extract in liquid form by physical or physico-chemical means in order to obtain a concentrated extract in dry form.

The harpagoside-concentrated organic phase preferably has a harpagoside titre greater than or equal to 5%.

According to an advantageous embodiment of the present invention, the organic solvent used in the purification step by a technique of the liquid-liquid extraction type is selected from the esters, especially the aliphatic esters, and more particularly from the $C_1$-$C_6$-, preferably $C_1$-$C_4$-alkyl acetates.

The organic solvent used for the liquid-liquid extraction step is preferably methyl acetate, ethyl acetate or butyl acetate.

Ethyl acetate is particularly preferred because it is the most common on an industrial scale, has a very low boiling point (77.06° C.) and is an alimentary solvent. Accordingly, ethyl acetate has the advantage of being a water-immiscible solvent which is permitted in foodstuffs and enables *harpagophytum* extracts to be purified and titres greater than or equal to 35% to be obtained.

The use of ethyl acetate allows the evaporation—drying operations to be carried out at a much lower temperature than when butanol, for example, is used. This reduction in temperature then enables degradation of the active ingredients to be limited. Accordingly, ethyl acetate (boiling point 77° C. at atmospheric pressure) and water form an azeotrope which boils at 70.4° C. at atmospheric pressure and at less than 40° C. under a vacuum of 0.1 bar.

In addition, the water-butanol azeotrope contains 42.4% water, while the water-ethyl acetate azeotrope contains only 8.5% water, which enables it to be recycled industrially for new purifications without additional treatment.

The selectivity of ethyl acetate in respect of the desired molecules, iridoid glucosides of *harpagophytum*, as well as the properties of said solvent on evaporation, make it possible to obtain extracts having very high titres (>35%), with a real industrial economic performance, for the production of product intended for food supplements.

The equipment used within the context of the step of purification by liquid-liquid extraction is any type which allows two liquids to be mixed, more particularly a stirred reactor or packed column and in particular of the centrifuge type, which equipment allows the two phases of the method to be harvested rapidly: the concentrated aqueous phase, depleted of harpagoside, and the organic phase loaded with harpagoside. The method allows more than 90% of the active ingredients present in the starting aqueous phase to be recovered.

Accordingly, starting from a crude extract in liquid form in aqueous phase, obtained either by crude extraction of the plant with water or by crude extraction with alcohol followed by removal of the solvent, or by redissolving the crude extract in powder form in water, a method of purification by liquid-liquid extraction can be carried out.

The present invention relates also to a method as defined above, characterized in that the crude extract of *Harpagophytum procumbens* is obtained by a process comprising a step in which a solvent of the aqueous alcoholic type composed of from 0 to 90% alcohol is brought into contact with dried lateral roots of *Harpagophytum procumbens*, especially by extraction, maceration, decoction or percolation, and a step in which the solvent is removed by solid/liquid separation, especially by filtration, by desolvation or by centrifugation, in order to recover said crude extract, and an optional step in which said crude extract is concentrated in order to obtain said crude extract in the form of a thick liquid containing from 2 to 50% dry matter.

The alcohol mentioned above that constitutes the solvent of the aqueous alcoholic type is preferably methanol or ethanol.

The present invention relates also to a method as defined above in which the conversion of the concentrated extract in liquid form by physical or physico-chemical means is carried out by removing the solvent in a stream of hot air, by drying, by atomization, by evaporation, by sublimation, by dehydration, or by adsorption on a support.

The present invention relates preferably to a method for preparing a concentrated extract of *Harpagophytum procumbens*, in liquid form, having a harpagoside titre greater than or equal to 5%, preferably from 35 to 50%, said method comprising:
- a purification step of the type liquid-liquid extraction between a crude extract of *Harpagophytum procumbens* in liquid form in aqueous phase and an organic solvent selected from the esters, in order to obtain an aqueous phase and a harpagoside-concentrated organic phase, and
- a step in which the solvent is removed from the organic phase obtained previously in order to obtain said concentrated extract in liquid form.

The present invention relates preferably to a method for preparing a concentrated extract of *Harpagophytum procumbens*, in dry form, having a harpagoside titre greater than or equal to 5%, preferably from 35 to 50%, said method comprising:
- a purification step of the type liquid-liquid extraction between a crude extract of *Harpagophytum procumbens* in liquid form in aqueous phase and an organic solvent selected from the esters, in order to obtain an aqueous phase and a harpagoside-concentrated organic phase,
- a step in which the solvent is removed from the organic phase obtained previously in order to obtain said concentrated extract in liquid form, and
- a step in which said concentrated extract in liquid form is converted by physical or physico-chemical means in order to obtain a concentrated extract in dry form.

The present invention relates also to extracts as obtained by carrying out the method of the invention as defined above.

The present invention relates to a concentrated extract of *Harpagophytum procumbens*, in liquid form, soluble in aqueous phase, having a harpagoside titre greater than or equal to 35%, preferably from approximately 35% to approximately 50%, especially from approximately 35% to approximately 45% and preferably from approximately 35% to approximately 40%.

The present invention relates also to a concentrated extract of *Harpagophytum procumbens*, in dry form, having a harpagoside titre greater than or equal to 35%, preferably from approximately 35% to approximately 50%, especially from approximately 35% to approximately 45% and preferably from approximately 35% to approximately 40%.

The present invention relates also to a pharmaceutical composition comprising as active ingredient a concentrated extract of *Harpagophytum procumbens*, in liquid or dry form, in association with a pharmaceutically acceptable carrier.

The present invention relates also to a food supplement comprising a concentrated extract of *Harpagophytum procumbens*, in liquid or dry form, in association with an acceptable carrier.

EXAMPLES

Example 1

1) Preparation of the Crude Extract:

The crude extract is prepared from a tonne of lateral roots of *harpagophytum*. The lateral roots are macerated in water, with stirring, for 2 hours. A step of separation between the plant and the solvent by successive filtering operations (600 µm, 100 µm, then 25 µm) is then carried out. The following step is a step of concentration in vacuo, which allows yet more solvent to be removed and makes it possible to avoid subsequently handling an excessively large amount of solvent. A crude extract in concentrated form is then obtained.

2) Purification:

The concentrate is extracted directly in liquid phase with 1000 liters of ethyl acetate using a continuous centrifugal extractor.

The organic phase is recovered, and the solvent is removed in vacuo.

A concentrate in aqueous phase is obtained and can be reduced to a powder, for example in a stirred reactor in vacuo.

The resulting product has a harpagoside titre of 35% measured by HPLC. It must be noted that the initial aqueous phase is depleted of harpagoside and contains less than 0.3% harpagoside.

Example 2

1) Preparation of the Crude Extract:

The crude extract is prepared from 1 kg of lateral roots of *harpagophytum*. The lateral roots are macerated in ethanol (70 vol %) at 65° C., with stirring, for 2 hours. A step of separation between the plant and the solvent by successive filtering operations (600 µm, 100 µm, then 25 µm) is then carried out. The following step is a step of concentration in vacuo, which allows yet more solvent to be removed and makes it possible to avoid subsequently handling an excessively large amount of solvent.

A crude extract in concentrated form is then obtained (200 ml).

2) Purification:

The concentrate is extracted directly in liquid phase with 1000 ml of ethyl acetate using a continuous centrifugal extractor (at 0° C.).

The organic phase is recovered, and the solvent is removed in vacuo.

A concentrate in aqueous phase is obtained and can be reduced to a powder, for example by lyophilization. Accordingly, within the context of this example, a powder is obtained (20 g).

The resulting product has a harpagoside titre of 55% measured by HPLC.

The invention claimed is:

1. A method for preparing an extract of *Harpagophytum procumbens* for consumption as a food product, wherein said extract is in liquid or dry form, and wherein the extract has a harpagoside titer from 5% to 50% w/w, said method comprising:
   i.) preparing a crude extract of *Harpagophytum procumbens* by extracting roots of *Harpagophytum procumbens* with water and/or ethanol to provide an aqueous crude extract and plant material;
   ii.) optionally filtering the plant material from the aqueous crude extract and removing the plant material from the crude aqueous extract to produce a crude filtered aqueous extract; and
   iii.) purifying the crude aqueous extract or the crude filtered aqueous extract by liquid-liquid extraction using an ester organic solvent, wherein the crude aqueous extract or the crude filtered aqueous extract is extracted with the ester organic solvent, and the ester organic solvent provides an ester organic phase containing the extract of *Harpagophytum procumbens*.

2. The method according to claim 1, wherein the ester organic solvent is ethyl acetate.

3. The method according to claim 1, further comprising:
   iv.) removing the ester organic solvent from the extract of *Harpagophytum procumbens* obtained in step iii.) to obtain the extract in concentrated liquid form, and optionally converting the liquid form into a dry form to provide the extract in dry form.

4. The method according to claim 1, wherein the crude extract is obtained by extraction of dried lateral roots of *Harpagophytum procumbens* with 0 to 90% ethanol to provide an initial extract, combining the initial extract with an ester organic solvent, removing the ester organic solvent by solid/liquid separation to provide the crude extract, and optionally concentrating the crude extract to obtain the crude extract in the form of a liquid containing from 2 to 50% dry matter.

5. The method according to claim 4, wherein the solvent of water and/or ethanol optionally includes methanol.

6. The method according to claim 3, wherein converting the concentrated extract in liquid form to the dry form product comprises removing water in a stream of hot air, by drying, by atomization, by evaporation, by sublimation, by dehydration, or by adsorption on a support.

7. The method of claim 1, wherein the purifying the crude extract comprises using continuous centrifugation extraction.

8. The method according to claim 4, wherein removing the ester organic solvent by solid/liquid separation comprises separation by filtration.

9. The method of claim 1, wherein the extract of *Harpagophytum procumbens* is suitable for incorporation into a foodstuff.

10. The method of claim 1, wherein the extract of *Harpagophytum procumbens* is extracted using solvents suitable for inclusion into a foodstuff.

11. The method of claim 1, wherein preparing the crude extract of *Harpagophytum procumbens* comprises extracting by mixing *Harpagophytum procumbens* with water and/or ethanol to produce an initial extract as the crude extract.

* * * * *